United States Patent [19]

Torres et al.

[11] Patent Number: 5,028,696
[45] Date of Patent: Jul. 2, 1991

[54] ION EXCHANGE AND SEPARATION METHOD

[76] Inventors: Anthony R. Torres, 1285 Sumac, Logan, Utah 84321; Elbert A. Peterson, 4405 Cambria Ave., Garrett Park, Md. 20896-0257

[21] Appl. No.: 263,737

[22] Filed: Oct. 28, 1988

[51] Int. Cl.[5] .................... C07K 15/28; C07K 3/22; C07K 3/20
[52] U.S. Cl. .................... 530/387; 530/416; 530/417; 210/635; 210/656; 210/674
[58] Field of Search .................... 530/416, 417, 387; 210/635, 656, 674

[56] References Cited

U.S. PATENT DOCUMENTS 4,493,907  1/1985  Hedrick et al. .................... 521/26

OTHER PUBLICATIONS

Scopes, Robert K., 1987, *Protein Purification: Principles and Practice*, Springer-Verlag, New York, pp. 156–167.
Peterson et al., 1984, Methods in Enzymology, 104: 113–133.

*Primary Examiner*—Margaret Moskowitz
*Assistant Examiner*—Keith C. Furman
*Attorney, Agent, or Firm*—Mallinckrodt & Mallinckrodt

[57] ABSTRACT

A method of separating charged molecules having different numbers of charges thereon includes the step of passing the molecules to be separated through ion-exchange material such as an ion-exchange chromatograpy column in normal manner so that molecules to be separated bind to the ion-exchange material. Displacer molecules are then passed through the ion-exchange column to selectively release certain of the molecules to be separated from the ion-exchange material, while others of the molecules to be separated remain bound to the material. Rather than the displacer molecules having charges of a similar sign to the molecules to be separated so that the displacer molecules bind to the ion-exchange material in place of certain of the molecules to be separated thereby releasing them, the displacer molecules have charges of the same sign as the ion-exchange material and opposite the sign of the molecules to be separated so that certain of the molecules to be separated bind to the displacer molecules in place of the ion-exchange material and are thus released from the ion-exchange material and flow from the ion-exchange material with the diplacers. Displacers of various numbers of charges may be sequentially passed through the ion-exchange material in ascending number of charge order to thereby selectively release molecules to be separated. The last remaining molecules to be separated may be released selectively with displacer molecules or, may be released in known manner such as by elution.

25 Claims, 2 Drawing Sheets

ION EXCHANGE AND SEPARATION METHOD

BACKGROUND OF THE INVENTION

1. Field:

The invention is in the field of separating charged particles or ions, particularly macro molecules such as proteins, through chromatography.

2. State of the Art:

Various types of chromatography columns are in use today for a variety of purposes. One use of such columns is in the separation of proteins. A commonly used method for protein separation involves ion-exchange chromatography on silica based, cellulose based, or agarose based columns. With such a column, a solution containing the protein or proteins to be separated is passed through the column, and the electrically charged proteins are captured by the oppositely charged ion-exchange adsorbent material of the column.

Once the proteins are adhered to the column, the proteins are removed from the column, preferably selectively, by either displacement or elution methods. The elution methods are most commonly used and involve either changing the pH of the buffer solution passing through the column or increasing the salt concentration in the buffer solution or both. When the pH of the solution is changed, the electrical charges on the proteins or on the ion-exchange adsorbent material in the column are changed and the proteins are released by the column. With an increase in background salt in the column, the salts break the bonds between the proteins and the ion-exchange adsorbent material in the column to similarly release the proteins. As the pH level is gradually changed or as the salt level is gradually increased, the proteins having the smaller number of electrical charges, i.e., of bonds to the column, will generally be released first and those with the larger number of charges will be released later. This is because it is more likely that, as individual bonds are broken, all of the bonds of a protein having fewer bonds will be broken first to release that protein. Band spreading is a problem in elution chromatography and the large volume of effluent necessary to accommodate this spreading is particularly burdensome on large columns. Usually, the volume of effluent is markedly reduced in large scale separations at the cost of lower resolution. Therefore, where good selectivity is needed, small columns with small quantities of proteins must be used.

With ion-exchange displacement methods of protein separation, the salt concentration and buffer pH in the column are kept constant while displacer molecules are passed through the column. The displacer molecules are chosen to have a number of like electrical charges exceeding the number offered by the protein to be released. The displacers are also chosen to have a higher affinity for the column material than the targeted proteins. In this way, when a displacer is introduced into the column, all proteins having the same or lesser charges are released. Then a displacer with a larger number of charges is introduced into the column to release proteins having charges in the range between the proteins initially released and those having a number of charges equal to those of the displacer. This process can be repeated with various displacers of increasing number of charges, as desired, to selectively release proteins in the column. Displacement provides good selectivity of the proteins released. However, while ion-exchange displacement is used frequently with anion-exchange columns because of the availability of anionic displacers, it is difficult to use ordinary displacement methods when the proteins have predominantly positive charges and are therefore adsorbed on cation-exchange columns for which anionic displacers have no affinity. Cationic displacers are not generally available and where available are very limited in variety, so ordinary displacement is not now practical with cation-exchange columns.

SUMMARY OF THE INVENTION

According to the invention, charged molecules or ions having a similar number of charges may be separated from charged molecules having a different number of charges of similar sign by passing the charged molecules to be separated through ion-exchange material having a charge polarity opposite to the polarity of the charge on the molecules to be separated. The molecules to be separated will attach to the ion-exchange material. Displacer molecules having a number of charges equal to or greater than the number of charges of some of the molecules to be separate but not as great as other of the molecules to be separated, and of the same polarity as the ion-exchange material, are passed through the ion-exchange material to attach to the molecules to be separated having the same or smaller number of charges thereon than the number of charges on the displacer molecules. The molecules to be separated that attach to the displacer molecules are thereby released from the ion-exchange material and flow from the ion-exchange material with the displacer molecules. The molecules to be separated remaining attached to the ion-exchange material may then be released from such material by standard methods such as elution, or, if molecules of varying charges remain on the ion-exchange material, the molecules may be selectively released by application of displacer molecules of successively greater number of charges.

By use of the invention, the advantages of displacement chromatography can be achieved in a cation-exchange column by the use of anionic displacers. In such instance, the displacers are chosen not so as to replace the protein bonded to the column, thereby releasing the protein while the displacer is bound to the column in its place, as is normally done, but by choosing the anionic displacer to effectively bond to the adsorbed proteins instead of to the column thereby releasing the protein from the column by bonding it to the displacer so that the protein and the displacer to which it is bonded flow from the column. Displacers may be chosen in the same manner as in normal displacement chromatography and are similarly selective in the proteins released.

While the invention is presently used and is described in connection with cation-exchange columns because ordinary displacement chromatography is not available, it can be similarly used with anion-exchange columns and cationic displacers. Further, while the invention is described in detail in connection with the separation of proteins, it can be applied to separation of charged particles or ions generally, as will be understood by those skilled in the art.

In a particular method of the invention wherein particular proteins, such as monoclonal antibodies, are to be separated and recovered and wherein it is undesirable to have the protein accompanied by displacer as it leaves the column, the displacers are used to release the impurities or unwanted proteins from the column while the desired protein remains bound to the column. After the impurities are removed by the displacement method of the invention, the desired protein left on the column is removed from the column by elution techniques to provide the purified protein. Being able to operate in this fashion under conditions in which the desired protein is the most firmly bound protein in the column (in contrast to being the least firmly bound on an anion-exchange column) very significantly increase the capacity of the system for purifying the desired protein and provides greater opportunity for increasing the selectivity of the process.

THE DRAWINGS

In the accompanying drawings, which show an embodiment of the invention presently contemplated as the best mode for carrying out the invention:

FIG. 1 is a schematic flow diagram illustrating an embodiment of the invention;

FIG. 2, a chart showing the output of the spectrophotometer of FIG. 1 showing an example of the separation of proteins achieved through use of the invention; and FIG. 3, a representation of the results of electrophoresis tests on samples of fluid collected by the fraction collector of FIG. 1 and corresponding to various portions of the spectrophotograph of FIG. 2.

DETAILED DESCRIPTION OF THE PREFERRED EMBODIMENT

Figure 1:
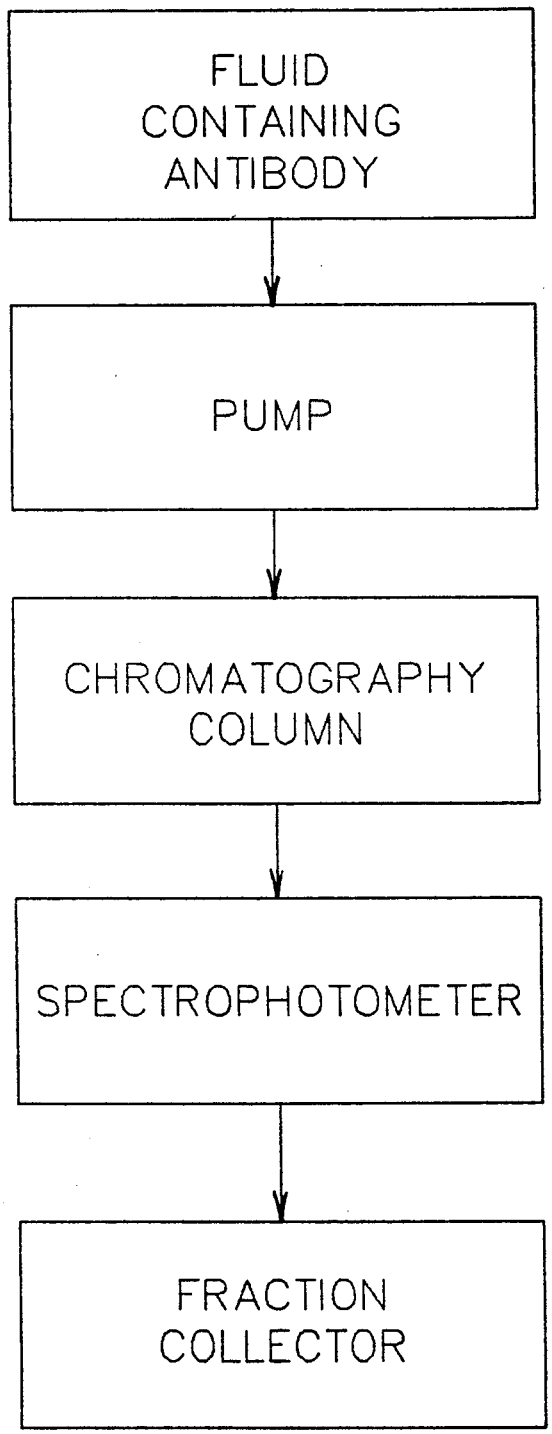

With the separation process of the present invention, as with prior art processes, a liquid having components therein to be separated wherein each of the components has a different number of electrical charges thereon of similar polarity, is fed through a chromatography ion-exchange column having oppositely charged ion adsorbent material therein so as to capture thereon the components to be separated. The column adsorbent is chosen so that the individual components to be separated will be bound to the column with different numbers of bonds or with different affinities for the column. With prior art displacement chromatography, a displacer of similar charge polarity to that of the components adsorbed by the column is fed through the column to replace the adsorbed components. Generally the displacer will have a charge thereon and an affinity for the column greater than that of some of the components adsorbed on the column but less than that of other components adsorbed thereon. Under such conditions, the displacer will replace or displace adsorbed components having the same or lesser number of charges than the displacer. By sequentially passing several displacers of increasing number of charges and affinity for the column through the column, the adsorbed components are selectively released from the column. Alternatively, a mixture of several displacers of increasing number of charges and affinity for the column may be passed through the column to selectively release the components from the column.

With the present invention, rather than using displacers having a charge of the same polarity as the charge of the components adsorbed on the column so that the displacer is adsorbed on the column in place of the components, thereby releasing the components as taught by the prior art, the displacer has the same polarity charge as the ion-exchange material in the column and is chosen to have a greater affinity for the components adsorbed on the column than the ion-exchange material or adsorbent of the column. Thus, with the displacers of the invention, rather than taking the place of the adsorbed components on the column, thereby releasing such components, the displacers take the place of the column and the components are adsorbed on the displacers and thereby released from the column. The released components bonded to the displacers then flow from the column. With the invention, displacers having different numbers of charges may be sequentially used to release components of different charges. Thus, a displacer having a certain number of charges will adsorb components from the column having the same or a lesser number of charges and thereby release such components from the column. A second displacer having a greater number of charges will then adsorb the components from the column having the same or lesser number of charges, which results in adsorption and release from the column of all of those components having a number of charges between the number of charges of the first displacer and the number of charges of the second displacer. Any number of displacers may be used sequentially in this manner to obtain selective release of components from the column.

The components released from the column and bound to the displacers may go through further processing to separate the component from the displacer, if necessary. In many cases such separation will not be necessary as the displacer will not be detrimental to further use of the component, or the component removed with the displacer will not be a desired component for further use.

Where it is desired to separate one component from the other components so as to purify the one component for further use and where it is undesirable for the desired component to be attached to a displacer, if the desired component is the most strongly bound to the column, i.e., it has the highest number of charges and, thus, the highest number of bonds to the column, the various undesired components can be removed from the column by means of displacement according to the invention leaving only the desired component bound to the column. The desired component can then be removed from the column by any prior art method such as by elution to remove the desired component without displacers attached thereto.

The method of the invention is particularly useful in the field of separating desired proteins from undesired or contaminating proteins, such as in purifying monoclonal antibodies, and the invention will be described in detail with reference to a particular example in that field.

Monoclonal antibodies, in many instances, are grown in ascites fluid or serum media containing various proteins in addition to the desired monoclonal antibodies. Such additional proteins usually include albumin and transferrin which have been found to be very difficult to separate from the monoclonal antibodies. Since many of these proteins are cationic, i.e., many are positively charged under the pH condition of the fluid needed for stability of the fluid and needed to provide optimal selectivity, normal displacement chromatography cannot be used to separate the proteins. This is because a cation-exchange column is needed to adsorb the positively charged proteins and satisfactory cationic displacers are not available to perform such separation.

With the present invention, the ascites fluid or serum in which the monoclonal antibodies are grown is passed through a cation-exchange column, such as a CM-cellulose column, which adsorbs the positively charged proteins from the fluid. Such positively charged proteins include not only the desired antibody, but transferrin and other undesired positively charged proteins. Most of the albumin and other protein impurities flow through the column without being retained. In this instance, the gamma-globulin, which contains the desired monoclonal antibodies, is the protein most tightly bound to the adsorbent material of the column, with other adsorbed proteins less tightly bound.

Since the gamma-globulin, the desired protein, is the most tightly bound, if an excess of proteins having positive charges are supplied to the column, the proteins with the lower number of charges will not compete for binding sites as effectively as proteins with more positive charges. Although this is a favorable event, protein protein displacement is not as effective as displacer protein displacement. However, the separation capacity can be increased by overloading the column with the unwanted proteins so that the proteins adsorbed and retained by the column are comprised largely of the desired gamma-globulin. The protein-coated adsorbent material in the column will then provide a positively charged surface for the frontal analysis of the anionic, negatively charged, displacers used in the invention, such as carboxymethyldextrans (CM-Ds). A succession of displacers of increasing charge and affinity may be fed through the column after the fluid containing the gamma-globulin to selectively release the proteins, if desired, or a displacer of affinity just below that of the desired protein or a mixture of displacers with affinities below that of the desired protein may be fed through the column after the fluid to release all but the desired proteins in a single step. When all but the desired protein has been removed from the column by the displacers, the desired protein can be sharply released with salt as in a normal salt elution of the column. This provides the separated or purified monoclonal antibodies.

When a mixture of proteins such as ascites fluid or serum is applied to a cation-exchange column such as a CM-cellulose column, at pH values that render many of the proteins cationic, those protein molecules which can present an adequate pattern of positive charges to the negatively charged adsorbent (cation-exchanger) will be adsorbed tightly. Others will be adsorbed lightly or not at all and will pass through the column slowly or rapidly, leaving behind a region of the column that presents a predominantly positive surface as a result of its being covered with relatively basic proteins. Within that region, the adsorbed proteins will have been more or less distributed in the order of decreasing affinity for the adsorbent as a result of competition among the various components (displacement). The efficiency of such displacement varies among proteins and the distribution is affected by such factors as the molecular weight of the protein and the permeablity of the adsorbent. Although such a preliminary separation is a favorable event, the separations to be obtained by subsequent operations do not require it.

Passage of a mixture of suitable, negatively charged polyanions, such as carboxymethyl-dextrans (CM-Ds), through the protein-coated CM-cellulose will result in a frontal analysis of the CM-Ds, the higher-affinity components of the CM-D mixture being adsorbed tightly to the basic proteins covering the adsorbent surface and the lower affinity CM-Ds moving on to be adsorbed at unoccupied sites on the protein until retarded higher-affinity CM-Ds reach and again displace them. Some CM-Ds may not be adsorbed at all. Other low-affinity CM-Ds may form complexes with adsorbed proteins, reducing the number of effective positive charges that can be offered by the protein molecules to the adsorbent to a level that is inadequate for continued adsorption, and the complexes move on. Still other CM-Ds will be firmly bound to proteins that remain tightly bound to the adsorbent. A competition between the CM-Ds and the adsorbent for binding sites on the proteins is involved, and, in order to remove all of the proteins, the highest-affinity CM-D employed must match, approximately, the most densely charged portions of the adsorbent chains. Although the adsorbent generally contains less than 1 meq of carboxyl groups per gram, the density of charge of the effective chains of the adsorbent is many times as high as that average, since most of the matrix is essentially unsubstituted. This is particularly true of CM-52, in which the carboxymethyl groups have been attached to cross-linked microcrystalline cellulose, allowing a higher incorporation to be attained on the surface chains without gelatinizing the adsorbent. The use of fibrous CM-cellulose having a lower content of carboxymethlyl groups (0.7 meq per gram or lower) may permit the release of even very basic proteins by CM-Ds having carboxymethyl group contents in our present range.

Since competition between the adsorbent surface chains and the CM-Ds for binding to the proteins is the operating principle, protein portions of the protein CM-D complexes that are released from the original band of proteins are readsorbed farther down the column on unoccupied adsorbent (or occupied by lower-affinity proteins) and again released when CM-D of adequate affinity for the protein reaches that site, generally as part of a protein CM-D complex. At each equilibration, both the CM-D and the protein that are released for further migration will tend to be of lower affinity than the corresponding molecules that remain adsorbed to that site. This repeated exchange of components between complexes permits an effective competition between proteins, almost as though they were being driven by a displacement train of polycations. Thus, the invention, in effect, produces the same result as the normal displacement chromatograph, but with the released proteins bound to a displacer molecule rather than being free.

While the cation-exchange column has been described as a CM-cellulose column, various cation-exchange columns may be used such as a sulphopropyl- or sulphoethylcellulose column or silica, agarose, or polymer columns. Further, while the displacers have been described as CM-Ds, various other displacers may be used such as carboxymethylcellulose, charged polysacharides, or synthetic charged polymers such as polyacrylate.

A preferred procedure for the method of the invention that has been found satisfactory in the separation of monoclonal antibodies and immunoglobulin from ascites fluid or serum is to equilibrate a carboxymethylcellulose column or other cation-exchange column with a buffer, such as a 20 mM histidine chloride solution at a pH between 5.3 and 5.7 with 5.7 preferred, or a sodium phosphate buffer solution at a pH between 6.1 and 6.5. Various other buffers such as MES or imidazole buffers may be used. The pH of the buffer will vary with the particular buffer solution used and will be adjusted for the particular buffer so that it provides good buffering action. The buffering solution is pumped through the column and it has been found that for proper preparation of the column a volume of buffer equal to about 10 to 20 column volumes should be used and should be pumped through the column at a rate of about 2-4 column volumes per hour.

The fluid or serum containing the monoclonal antibodies is prepared by diluting the salt out by a factor of about 10 and placing the fluid or serum in a buffer base. Generally this can be done by adding 1 ml of ascites fluid or serum containing the monoclonal antibody (usually will contain between 1-15 mg of monoclonal antibodies) to 2 ml of 0.1M histidine base. Hydrochloric acid is then added to bring the pH to 5.7 and water added to bring the total volume to 10 ml. Alternately, the fluid can be prepared by dialysis to reduce the salt level. Dialysis involves passing the fluid through membranes through which the salt can pass but the proteins cannot. The dialyzed proteins are adjusted to the desired pH with the histidine chloride buffer.

The displacer is prepared by making a 0.5-2.0% (most commonly 1-1.5%) CM-Dextran solution with RPV about 25 in a buffer such as 20 mM histidine chloride. The RPV value or reciprocal of pellet volume is a measure developed by the inventors to measure the number of carboxyl groups on the dextran and give an indication of the number of charges for the CM-Dextran. The RPV value is described in an article entitled "Ion-Exchange Displacement Chromatography of Proteins, Using Narrow-Range Carboxymethyldextrans and a New Index of Affinity", in *Anal. Biochemistry* 130:271-282, 1983.

A preferred embodiment of apparatus is shown schematically in the flow diagram of FIG. 1. The fluid containing the antibody to be separated is in a container connected to a pump such as a peristaltic pump manufactured by ISCO of Lincoln, Nebr. and sold under the trademark TRIS. The pump pumps the fluid to the chromatography column. The effluent from the column flows through a UV absorbance photometric detector such as a UA5 Spectrophotometer manufactured by ISCO which operates at a wavelength of 280 nm. The effluent then flows to a fraction collector such as an ISCO FOXY fraction collector which separates the effluent on either a volume or time basis.

The prepared solution containing the monoclonal antibodies to be separated is pumped into the prepared chromatograph column followed by a buffer such as 20 mM histidine chloride with buffer being passed through the column until the unbound proteins have passed through the column and absorbance shown by the detector is at baseline. This usually requires about 2-4 column volumes of buffer. The 1-1.5% prepared displacer in a volume equal to about 1-2.5 times the column volume is passed through the column followed by buffer such as the 20 mM histidine chloride to remove the unwanted proteins from the column. About 2-6 column volumes of this buffer is preferred. The monoclonal antibody, and minor impurities remaining on the column, are now eluted from the column by 0.15M NaCl in 10 mM sodium phosphate solution with a pH of 7.5, using about 5 column volumes.

In a specific example, 65 ml of ascites fluid containing $IgG_{2b}$ monoclonal antibodies was added to 120 ml 0.1M histidine base. Hydrochloric acid was added to bring the pH to 5.7 and water was added to bring the total volume to 600 ml.

The column used was a 160 ml column made by Kontes, Vineland, N.J. which was packed with CM-52 as made by Whatman, Inc., of Clifton, N.J. The column was equilibrated with 20 mM histidine chloride buffer at pH 5.7 as indicated above. The prepared liquid containing the monoclonal antibodies was pumped through the column at the rate of 3 column volumes/hr (480 ml), followed by 20 mM histidine chloride buffer at the same rate for one hour. After this, 280 ml of 1.5% CM-D with RPV=25 in 20 mM histidine chloride buffer at pH 5.7 was pumped through the column as the displacer at the rate of 480 ml per hour, followed by 2 column volumes (320 ml) of 20 mM histidine chloride buffer at the same rate of 480 ml per hour. The column was then eluted using 0.15M NaCl in 10 mM sodium phosphate solution, pH 7.5, at the rate of 480 ml per hour for 7 column volumes. The effluent from the column was measured using flow-through spectrophotometry and SDS-polyacrylamide gel electrophoresis and the results are shown in FIGS. 2 and 3.

Figure 2:
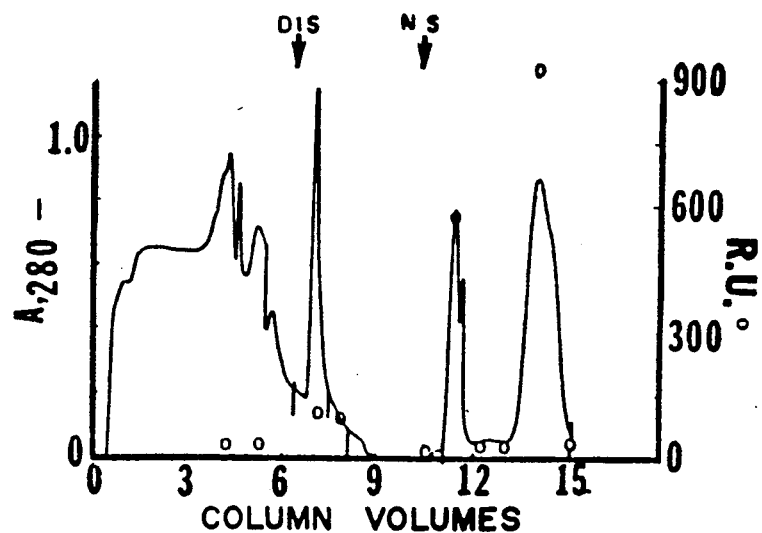

FIG. 2 shows the results of the flow-through spectrophotometer measurements which show absorbence by the effluent from the column of light of a wavelength of 280 nm. The amount of absorbence is shown on the verticle axis in units shown along the left vertical axis. The horizontal axis is calibrated in column volumes of material flowing through the column. Thus, the number "3" indicates that three column volumes or 480 ml (160 column volumes ×3) of liquid have flowed through the column. The zero is the point after equilibration of the column that the liquid containing the antibodies is first introduced into the column. In the example described and shown in FIG. 2, three column volumes of the liquid is pumped through the column followed by three column volumes of buffer. Thus, the "3" indicates the point at which the flow of liquid with antibodies stopped and the flow of buffer began. The output is delayed somewhat because of the time it takes for the liquid to flow through the column. The "6" represents the stopping of flow of buffer and start of flow of displacer solution through the column, indicated by the arrow labeled DIS. 280 ml or 1.75 column volumes of displacer was pumped through the column so the distance on the horizontal axis representing 7.75 column volumes is the stopping point of the displacer solution and the start of flow of buffer again. Two column volumes of buffer followed the displacer solution and then the sodium chloride in sodium phosphate solution is flowed through the columns to elute it. This solution starts flowing at about 10.75 column volumes as indicated by the arrow labeled NS, and flows to the end of the chart at 15.

The initial peak in FIG. 2, which represents the flow of the liquid containing the antibodies and the initial flow of buffer thereafter, contains unbound albumin. The second peak, representing the flow of the displacer through the column, shows removal of the initially adsorbed transferrin and other proteins that are displaced and flow from the column during the displacement. That displacement is actually taking place in the column rather than elution during flow of the displacer is indicated because transferrin and other bound proteins are released under conditions of pH and conductivity not compatible with elution. The pH actually drops to 5.3-5.5 with the addition of the displacer due to the collapse of the electrostatic shield on the ion-exchange material. The conductivity rises slightly but stays below the value of the diluted ascites fluid applied to the column. Together, these results are not compatible with elution by pH or salt. The third peak, which results just after the start of flow of the sodium chloride in sodium phosphate solution, shows the release of additional impurities. It is believed that these contaminants are released by the presence of the salt. The fourth peak, occurring later during flow of the sodium chloride in sodium phosphate solution through the column, contains the monoclonal antibodies and small amounts of contaminants. The antibodies are released by an increase in pH caused by the salt solution. This change of pH lags the actual application of the salt solution to the column which should explain the existence of the two peaks during application of the salt solution.

Figure 3:
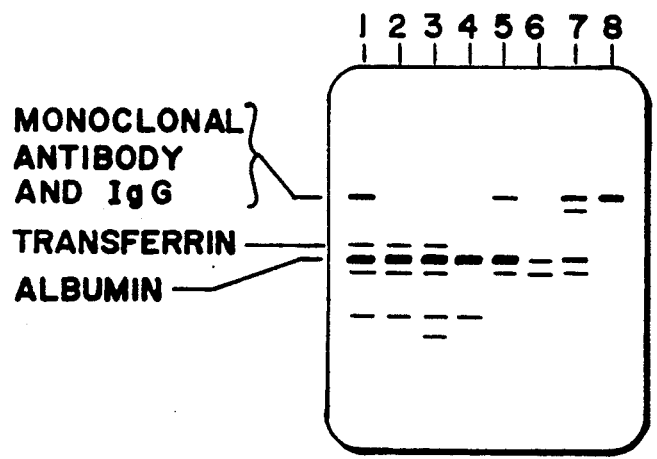

The actual composition of the peaks of FIG. 2 as revealed by gel electrophoresis is shown in FIG. 3. Samples of 0.5 µl each of the effluent from the column were taken at various times and subjected to electrophoresis using the Pharmacia standard Phast Gel system using a 10-15% gradient SDS gel. Lane 1 in FIG. 3 represents a sample of fluid prior to passing through the chromatography column and is used as the standard. Lanes 2, 3, and 4 represent samples taken during the first peak of FIG. 2. The position of the major material shows that it is albumin. The position of the stained material in lanes 5 and 6, from samples taken during the second peak in FIG. 2, identifies that material as transferrin. The stained material in lane 7, from a sample taken from the third peak of FIG. 2, shows the third peak contains additional impurities, mainly transferrin as well as some gammaglobulin (antibodies). The position of the dyed material in lane 8, from a sample taken from the fourth peak of FIG. 2, identifies the material as the desired monoclonal antibodies, plus some minor impurities shown by the dyed material just below the top protein band. The identification of the monoclonal antibody was confirmed by an immunological assay on a Beckman ICS Rate Nephelometer, the nephelometer readings being shown as open circles in FIG. 2. The units on the right hand vertical axis in FIG. 2 indicate the measurement values of the nephelometer readings in rate units. The reading of about 900 directly over the fourth peak confirms that the fourth peak contains the desired antibodies. Lane 8 also shows an absence of transferrin indicating that the transferrin has been separated from the antibodies. The absence of transferrin in lane 8 from peak 4 is significant as researchers have had difficulty getting highly purified monoclonals free of transferrin by prior art cation-exchange chromotography. A process described in an article entitled "A Method Suitable for the Isolation of Monoclonal Antibodies from Large Volumes of Serum Containing Hybridoma Cell Culture Supernatants" by Bo Malm appearing on pages 103-109 of Volume 104, 1987, of the *Journal of Immunological Methods*, requires that the antibodies separated by cation-exchange chromatography be passed through a gel filtration column (Sephacryl S-200 HR) to remove what appears from the article to be transferrin and albumin impurities which were not removed by the chromatography. FIGS. 2 and 3 show that even though some impurities remain with the desired antibodies, the separation of the albumin, transferrin, and the desired antibody is very good and the purity of the antibody obtained is about 90+% and well within the purity level normally needed. The separation of the albumin and transferrin is better than with other currently known methods of separation when used for isolating this particular antibody.

If greater purity is needed, additional high affinity displacers can be added before elution.

Similar experimental results have been obtained for $IgG_{2a}$, $IgG_1$, and $IgG_3$ monoclonal antibodies, using similar procedures to those described above. Polyclonal antibodies have also been purified from serum using similar procedures The CM-Ds used with the invention as the displacers can vary considerably in molecular weight, but generally fall within the range of from about 3,000-40,000. As the molecular weight gets larger, the molecular chains get longer, slowing diffusion and the attainment of equilibrum. They also do not work as well in gel electrophoresis. If the CM-Ds are too short, the concentration of CM-Ds becomes the operating factor rather than the number of charges per molecule. In such case, the affinity of the CM-Ds and their displacement characteristics will be lost. The preferred range is 5,000 to 15,000 with about 9,000 being preferred for particular applications in separating monoclonal antibodies from impurities. For other applications, larger or smaller displacer molecules may be preferred.

While the specific example of the invention described utilizes the displacement step and then an elution step, the elution step is not a required part of the invention and other methods of removal of the molecules could be used or all of the molecules to be separated could be removed from the column by successive displacements. Further, changes in the specific conditions, times, and reagents used in carrying out the method may change the specific results obtained. For example, the amount of buffer (20 mM histidine chloride) added after the displacer and before the eluant (0.15 sodium chloride with 10 mM sodium phosphate) has been found to change the spread of the eluted proteins, i.e., the distance between peaks 3 and 4. Thus, such aspects of the method must be adjusted for the results desired.

Whereas this invention is here illustrated and described with specific reference to an embodiment thereof presently contemplated as the best mode of carrying out such invention in actual practice, it is to be understood that various changes may be made in adapting the invention to different embodiments without departing from the broader inventive concepts disclosed herein and comprehended by the claims that follow.

We claim:

1. A method of separating charged molecules having a similar number of charges from molecules having a differing number of charges wherein the molecules are contained together in a fluid, comprising:

A. passing the fluid containing the molecules to be separated through ion-exchange material having a charge of opposite polarity to the charges on the molecules to be separated so that the molecules to be separated attach to the ion-exchange material;

B. passing displacer molecules having a number of charges equal to or greater than the number of charges of some of the molecules to be separated but not as great as others of the molecules to be separated and such charges being of opposite polarity to the molecules to be separated and of the same polarity as the ion-exchange material, through the ion-exchange material to attach to the molecules to be separated having the same or smaller number of charges thereon than the number of charges on the displacer molecules, there being no specific interaction of the displacer molecules with any of the molecules to be separated, the interaction being solely ion-exchange in nature, whereby the molecules to be separated having the same or smaller number of charges thereon than the number of charges on the displacer molecules are released from the ion-exchange material and attach to the displacer molecules and flow from the ion-exchange material with the displacer molecules as a first group, leaving molecules to be separated having a greater number of charges attached to the ion-exchange material; and C. releasing the molecules remaining attached to the ion-exchange material from the ion-exchange material separately from the first group whereby the molecules to be separated are separated into at least two groups.

2. A method according to claim 1, wherein the step of releasing the molecules remaining attached to the ion-exchange material from the ion-exchange material separately from the first group includes at least one additional step of passing displacer molecules through the ion-exchange material, each successive step using displacer molecules having a number of charges greater than the displacer molecules used in the previous step to attach to the molecules to be separated having a number of charges greater than the number of charges on the displacer molecules of the previous step and equal to or less than the number of charges on the displacer molecules of the current step; and releasing the molecules, if any, remaining attached to the ion-exchange material separately from the successive steps applying the displacer molecules.

3. A method according to claim 2, wherein the step of releasing the molecules, if any, remaining attached to the ion-exchange material includes the step of elution of bound material to cause release of the remaining molecules.

4. A method according to claim 1, wherein the step of releasing the molecules remaining attached to the ion-exchange material from the ion-exchange material separately from the first group includes the step of elution to cause release of the remaining molecules without displacer molecules attached thereto.

5. A method according to claim 1, wherein the charged molecules to be separated are proteins.

6. A method according to claim 5, wherein the fluid containing the molecules to be separated is a fluid in which monoclonal antibodies are grown and the molecules to be separated include monoclonal antibodies and other proteins.

7. A method according to claim 6, wherein the molecules which flow from the ion-exchange material with the displacer molecules as a first group are the molecules other than the monoclonal antibodies and the molecules left attached to the ion-exchange material are the monoclonal antibodies.

8. A method according to claim 7, wherein the step of releasing the monoclonal antibodies from the ion-exchange material includes the step of elution to release the antibodies therefrom without displacer molecules attached thereto.

9. A method according to claim 8, wherein the ion-exchange material is a cation-exchange column.

10. A method of separating a plurality of proteins wherein different proteins to be separated have a different number of like signed charges thereon and are contained in a fluid, comprising:

A. passing the fluid containing the proteins through a chromatography column having an ion-exchange material therein having a charge of opposite polarity to the charges on the proteins to be separated so that the proteins to be separated attach to the ion-exchange material in the column;

B. passing displacer molecules having a number of charges equal to or greater than the number of charges on some of the proteins to be separated but not as great as other of the proteins and of the same polarity as the ion-exchange material and opposite the polarity of the proteins attached to the ion-exchange material, through the ion-exchange material to attach to the proteins having a number of charges equal to or less than the number of charges on the displacer molecules, there being no specific interaction of the displacer molecules with the proteins to be separated, the interaction being solely ion-exchange in nature, whereby such proteins are released from the ion-exchange material and attach to the displacer molecules and flow from the column with the displacer molecules as a first group, leaving proteins having a greater number of charges attached to the ion-exchange material in the column; and C. releasing the proteins remaining attached to the ion-exchange material from the ion-exchange material in the column separately from the first group whereby the proteins to be separated are separated into at least two groups.

11. A method according to claim 10, wherein the proteins to be separated have positive charges thereon and wherein the chromatography column is a cation-exchange column.

12. A method according to claim 11, wherein the column is a carboxymethylcellulose column.

13. A method according to claim 12, wherein the displacer molecules are carboxymethyldextran molecules.

14. A method according to claim 13, wherein the fluid containing the proteins to be separated is a fluid in which monoclonal antibodies are grown, wherein the proteins to be separated include monoclonal antibodies, wherein the monoclonal antibodies are to be separated from other proteins in the fluid, and wherein the process includes the steps of preparing the fluid containing the proteins by diluting the salt in the fluid and providing a buffer base for the fluid prior to passing the fluid through the ion-exchange material.

15. A method according to claim 14, wherein the fluid is ascites fluid.

16. A method according to claim 14, wherein the salt is diluted by a factor of about ten.

17. A method according to claim 14, wherein the fluid is adjusted to have a pH value of about 5.7.

18. A method according to claim 17, including the step of passing a buffer solution through the ion-exchange material after passage therethrough of the prepared liquid containing the molecules to be separated but before passage therethrough of the displacer molecules.

19. A method according to claim 18, wherein enough buffer is passed through the ion-exchange material to remove substantially all unbound molecules from the ion-exchange material.

20. A method according to claim 19, wherein 2-4 chromatography column volumes of buffer are passed through the ion-exchange material.

21. A method according to claim 18, wherein the displacer molecules are placed in a buffer solution at a concentration of between about 0.5-2.0% prior to passing the displacer molecules through the ion-exchange material.

22. A method according to claim 21, wherein the displacer molecules are chosen to bind to proteins other than the monoclonal antibodies bound to the ion-exchange material to thereby release proteins other than the monoclonal antibodies from the ion-exchange material as the first group and to leave the monoclonal antibodies bound to the ion-exchange material.

23. A method according to claim 22, including the step of passing a buffer solution through the ion-exchange material after passage therethrough of the displacer molecules.

24. A method according to claim 23, wherein the proteins remaining bound to the ion-exchange material after passage therethrough of the displacer is released from the ion-exchange material by the step of elution whereby the monoclonal antibodies are separated from the other proteins and are released from the ion-exchange material as a second group and without being bound to displacer molecules.

25. A method of purifying monoclonal antibodies by separating the monoclonal antibodies from unwanted proteins in a fluid in which the monoclonal antibodies are grown, comprising the steps of preparing the fluid in which the monoclonal antibodies are grown for passage through an ion-exchange chromatography column; passing the prepared fluid containing the monoclonal antibodies through an ion-exchange chromatography column chosen to adsorb the monoclonal antibodies; preparing a solution of displacer molecules wherein the displacer molecules are selected to adsorb and bind to proteins other than the monoclonal antibodies; passing the prepared solution of displacer molecules through the ion-exchange column after the fluid containing the monoclonal antibodies has been passed therethrough whereby the displacer molecules will adsorb and bond to protein molecules previously adsorbed by the column other than the monoclonal antibodies thereby releasing the protein molecules other than the monoclonal antibodies from the column so that they flow from the column with the displacer molecules; and then removing the monoclonal antibodies remaining adsorbed on the column from the column without the unwanted proteins that were previously removed from the column.

* * * * *